United States Patent [19]

Hamas

[11] 4,264,990
[45] May 5, 1981

[54] MAMMARY PROSTHESIS

[76] Inventor: Robert S. Hamas, 7070 Forward Ave., Apt. 808, Pittsburgh, Pa. 15217

[21] Appl. No.: 53,051

[22] Filed: Jun. 28, 1979

Related U.S. Application Data

[63] Continuation-in-part of Ser. No. 6,117, Jan. 24, 1979, abandoned.

[51] Int. Cl.³ .............................................. A61F 1/03
[52] U.S. Cl. ......................................................... 3/36
[58] Field of Search .................................................. 3/36

[56] References Cited

U.S. PATENT DOCUMENTS

| | | | |
|---|---|---|---|
| 146,805 | 1/1874 | Cox | 3/36 X |
| 1,417,930 | 5/1922 | Mailleue | 3/36 |
| 3,663,968 | 5/1972 | Mohl et al. | 3/36 |
| 3,852,832 | 12/1974 | McGhan et al. | 3/36 |
| 3,852,833 | 12/1974 | Koneke et al. | 3/36 |
| 3,934,274 | 1/1976 | Hartley, Jr. | 3/36 |

Primary Examiner—Clifford D. Crowder
Attorney, Agent, or Firm—Webb, Burden, Robinson & Webb

[57] ABSTRACT

This invention relates to a mammary prosthesis and a method of implanting same. The prosthesis comprises a flexible backing and a soft front envelope, for example, of the inflatable or prefilled type. The flexible backing defines, at least one internal passageway or compartment into which rigidifying material may be forced or emplaced. Upon setting of the rigidifying material in the passageways or compartments, the backing loses a substantial part, if not all, of its flexibility. The rigidified backing thereafter prevents the contracture of natural fibrous tissues generated around the front envelope and backing in a way to prevent hardening of the prosthesis and/or palpable prosthesis edges prevalent with prior art devices.

33 Claims, 14 Drawing Figures

MAMMARY PROSTHESIS

RELATED APPLICATION

This application is a continuation-in-part of application Ser. No. 6,117, filed Jan. 24, 1979, now abandoned.

BACKGROUND

Breast prostheses have been available to increase breast size (augmentation) and to restore the breast mound in reconstruction procedures following mastectomy. The prostheses typically have an outer shell or envelope of thin silicone elastomer and are either pre-filld with a silicone elastomer "gel" or are filled with a saline solution through a tube and valve after implacement. The prostheses are available in numerous sizes (volumes), several shapes including tear drop, round, low-profile, etc. Some have Dacron patches on the back to allow fibrous tissue ingrowth causing the prosthesis to be adherent to the chest wall or pectoralis muscle. Usually prostheses are implanted via a small inframammary or peri-aerolar incision into a pocket dissected deep to the patient's own breast tissue in front of the pectoralis muscle. In certain circumstances, such as reconstruction after mastectomy, the prosthesis may be placed behind the pectoralis muscle.

In all cases, the prosthesis is surrounded by a natural "capsule" composed of fibrous scar tissue after it has been implanted for some period of time. This is a normal tissue reaction to the presence of a foreign body. Scar normally undergoes contracture during the healing process. This capsule of scar tissue contracts to variable degrees in all patients to deform the prosthesis toward a sperical shape to minimize the ratio of capsule surface area to volume of breast prosthesis. The contracture of the capsule may be slight so that the breast feels soft (i.e., natural) when examined or it may so compress the silicone elastomer gel or saline contents of the prosthesis that the breast will feel quite hard (i.e., unnatural) when examined. Where any given augmented breast falls on the spectrum from soft to hard depends upon the patient's own scar conracture process in trying to decrease the ratio of capsule surface area to volume of breast prosthesis. It has been reported that flexible silicone backings placed behind the soft front envelope result in a softer breast mount. However, since the backings were not rigid, they tended to curl up against the front envelope due to scar capsule contraction when placed in the usual location over the pectoralis muscle. Rybka and Cocke "The Value of Silicone Dacron-Felt Discs in Prevention of Capsular Contractions" *Plastic Surgical Forum,* Vol. 1, p. 221 (1978).

A basic requirement of any mammary prosthesis is that it can be inserted through a three to four centimeter incision. Hence, the backing cannot be rigid until implanted in a pocket behind the breast. Further the edges of the backing of the implant must not be palpable. A backing member must contour itself to the chest wall and/or the pectoralis muscle over which it is laid so that it does not rock back and forth. The prosthesis should not interfere with chest X-rays and mammography.

Two patents which relate to mammary prostheses are U.S. Pat. Nos. 3,293,663 and 3,934,274.

SUMMARY OF THE INVENTION

Briefly, according to this invention, there is provided a mammary prosthesis comprising a soft front envelope portion being the typical inflatable or prefilled silicone elastomer type and a flexible backing of an inert polymeric material which backing defines passageways and/or compartments into which a material may be injected or already emplaced to rigidify the backing. Preferably, the material is selected to set or harden and the backing is thus rigidified and resists warping or buckling. The rigidifying filler must be harmless and inert to tissue if perchance it leaks during the filling process or is exposed by a later tear in the envelope. Preferably, the front envelope is fixed to the flexible (prior to rigidification) backing although this is not an absolute requirement.

The method according to this invention comprises using the established surgical techniques to implant the unique prosthesis described herein. An incision is made either inframammary or peri-aerolar and the prosthesis described in the preceding paragraph is worked into position either against the chest wall or over the pectoralis muscle. Just before or after the prosthesis has been inerted and positioned to the surgeon's satisfaction, a rigidifying material, for example, a methyl methacrylate bone cement is forced into passageways and/or compartments provided in the flexible backing.

If the passageways and/or compartments of the backing are prefilled, this filling step is eliminated. However, in that case the rigidifying material must be activated to harden either just before the prosthesis is inserted or after it has been inserted. Activation may take place by exposure to ultraviolet light, for example. Typically, cements take about ten minutes to harden or set. The flexible backing with the unset cement therein may be molded to the chest or, at least, urged into a spheroidal shape having the concave portion thereof facing the chest. The molded backing is restrained by hand pressure or equivalent until setting of the rigidifying material takes place. Thereafter, if the front envelope portion of the prosthesis is not a prefilled envelope or was not already inflated in place, the envelope is inflated.

The applicant's invention increases the ratio of surface area of the scar capsule to volume of breast prosthesis by one or more of several techniques. Principally applicant's invention provides a rigid backing to the breast mound portion of the prosthesis (referred to herein as the front envelope) which will reduce the amount of possible contracture toward the spherical shape. The surface area to breast prosthesis volume is further increased by causing the backing to achieve a spherical shell configuration with the concave portion facing toward the chest. In a preferred embodiment, a backing defines a thin, rigid collar outwardly of part or all of the front envelope portion to increase greatly the potential surface area of the capsule while keeping the volume of the breast mound or front envelope portion of the prosthesis the same. This collar must be rigid so that the scar contracture process will not pull it up onto the front envelope portion of the prosthesis and thereby negate its effect in increasing the surface area of the capsule. This particular embodiment might not be used with a very thin patient with minimal subcutaneous tissues as edges of the collar might be palpable. The collar provides a space into which the front envelope portion of the prosthesis may flow when the patient moves or changes position to thus provide a more natural appearance.

Disclosed herein are a plurality of preferred embodiments which are explained in th detailed description which follows.

DRAWINGS

Further features and other objects and advantages of this invention will become clear from the following detailed description with reference to the drawings in which FIG. 1 is a side view of a prosthesis according to this invention;

Figure 11:
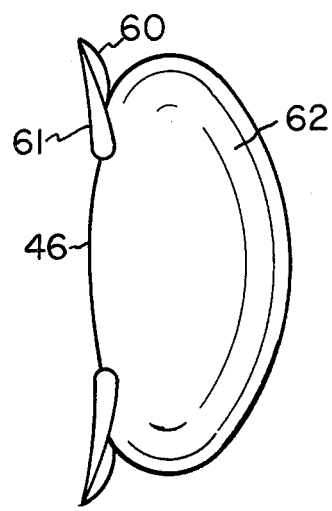
Figure 12:
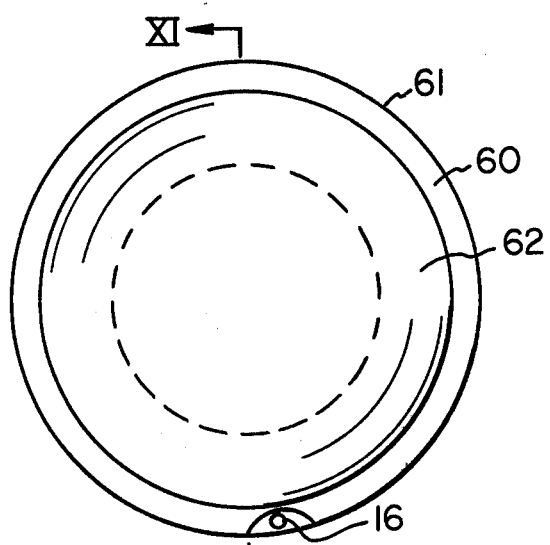
Figure 13:
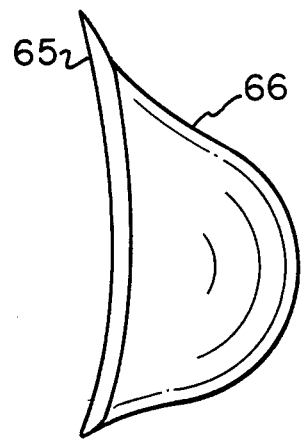
Figure 14:
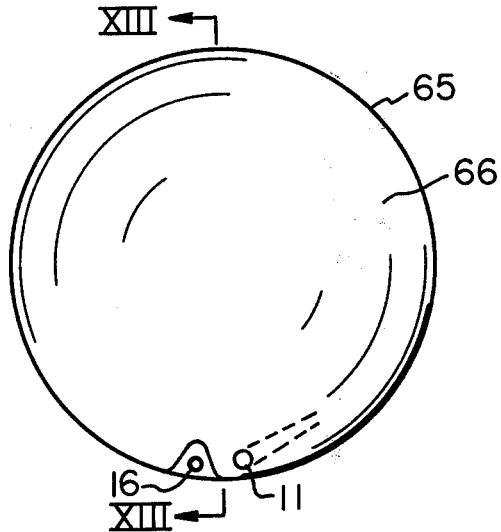

FIGS. 11 and 12 are sectioned side and front views of a prosthesis according to this invention in which the flexible backing is an annular disc having a second soft envelope positioned around the periphery of the front face thereof; and FIGS. 13 and 14 are sectioned side and front views of a prosthesis according to this invention in which the front envelope of the implant is generally tangent to the flexible backing at the outer periphery.

DESCRIPTION OF PREFERRED EMBODIMENTS

Figure 1:
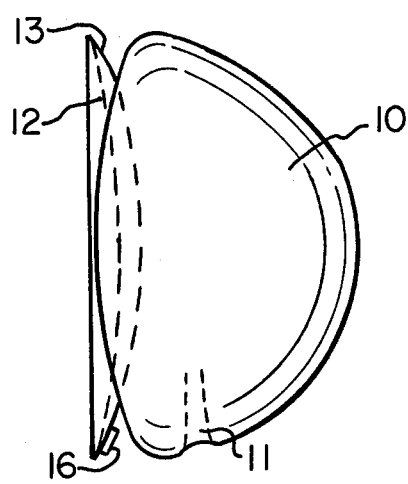
Figure 2:
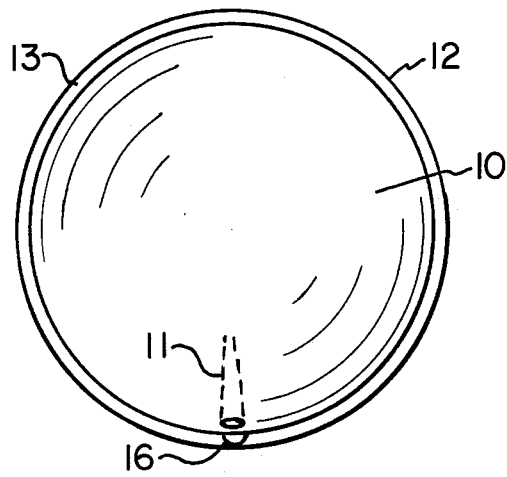
FIG. 2 is a frontal view of the prosthesis according to this invention and corresponding to FIG. 1.

Referring now to FIGS. 1 and 2, there is shown a mammary prosthesis according to this invention comprising a front envelope 10 which is a silicone elastomer envelope or the like either prefilled, for example with a silicone gel, or provided with a valve 11 such that it may be inflated after implacement with a saline solution or the like as is the typical practice. A flexible backing 12 is shown having a thin disc shape and in this embodiment being generally of greater outer dimension than the soft implant 10 thus providing a collar or flange 13 surrounding the front envelope. The shape and outer dimensions of the backing are variable and may, for example, be round having a diameter from 7 to 20 centimeters. Other shapes having curved edges, e.g., parabolic or oval are suitable. The flexible backing is constructed of silicone plastic, elastomer or the like which is not biologically reactive with the human body. The flexible backing must be sufficiently inelastic such that as the rigidifying material is being forced into the passageways and/or compartments thereof the backing does not bulge and deform and thus impede flow to all volumes of the passageways and compartments.

Figure 3:
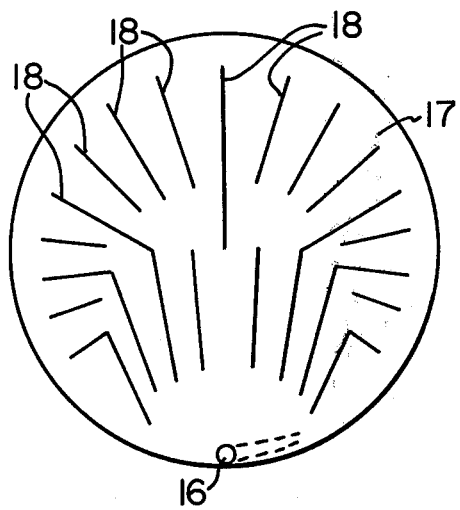
FIG. 3 is a front view of an embodiment of a flexible backing in which the backing is comprised of a thin flat envelope of flexible elastomer that is "quilted" to provide separate compartments for receiving rigidifying material.

FIG. 3 illustrates an embodiment of this invention in which the flexible backing material may be made of the same material from which the front envelope is made or some very similar material. This silicone elastomer is formed into a thin wall (e.g., 1 mm thick) envelope 17 having a plurality of elongate joins 18 as does a quilt but, of course, without stitching. The joins are formed by welding, bonding, or the like. Preferably, the quilts do not extend entirely to the periphery of the envelope thus enabling an uninterrupted ring of rigidified material around the periphery. At least one inlet port 16 is provided along with suitable air bleeds, if desired. With this embodiment, air bleeds are not necessary as the envelope enclosure may be completely aspirated prior to filling with rigidifying material. In all of the disclosed embodiments, but especially this embodiment, the volume of the rigidifying material contained by the compartments and/or passageways must not be excessive, i.e., more than needed to rigidify the backing. Otherwise, the heat of reaction of the setting filler (cement) will deform the backing and/or burn the patient. The passageways or compartments should provide a large surface to volume ratio (be thin) to minimize the heat transferred to any given area of adjacent tissue. It is desirable that at least one side of the backing envelope be fabric reinforced to prevent stretching of that side during the time rigidifying filler is being added.

Figure 4:
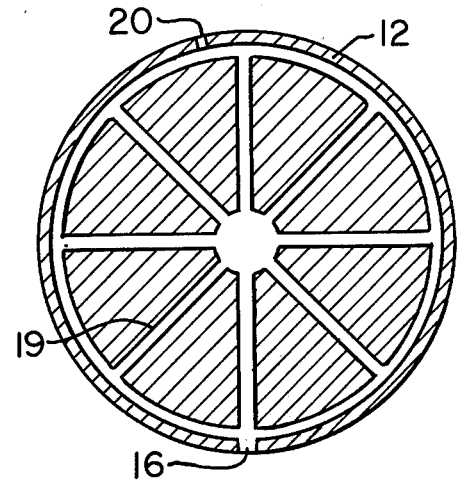
FIG. 4 is a front view of another embodiment of a flexible backing according to this invention sectioned to illustrate the passageways for receiving rigidifying material.

With reference to FIG. 4, another embodiment in which the backing 12 is a flexible plastic is illustrated. The flexible plastic backing has internal passageways 19 therein along with an inlet port 16 and at least one air bleed 20. The thickness of the backing may vary from about 2 to 15 millimeters with the passageways preferably at least about 2 millimeters in diameter. The backing is rigidified after implanting by forcing cementitious material into the passageways through the port 16. The air bleed 17 allows for the escape of air which would otherwise be entrapped in the passageways. The position of the port at the peripheral edge of the backing is acceptable for the implacement by an inframammary incision. The diameter of the air bleed is such that the viscosity of the rigidifying material prevents it from flowing out of the bleed (or bleeds). The ports to the passageways are suitably the same diameter as the passageways and may be slightly tapered outwardly to receive a funnel shaped tube or the like through which the material is forced into the passageways of the backing. According to a preferred embodiment, the port is designed for a bayonet connection with the tube through which the rigidifying material is to be injected. In some embodiments, it may be desirable to provide a check valve in the port permitting inflow of material but not backflow. After setting, the filler has no tendency to flow out of the backing and hence there is no need for a valve at that time. However, care must be taken to at least temporarily plug the port after filling but before setting of the material if pressure placed on the backing to cause it to conform to the chest would cause extrusion of the material out of the port. The flexible plastic backings, according to this embodiment, must be fabricated with passages. They may be fabricated from two or more thin (flexible but not elastic) plastic sheets, e.g., 2 to 7 millimeters with the passageway routed out of one surface. The sheets are then welded, bonded, glued together in a manner to create passageways only accessible from one port per passageway.

Figure 5:
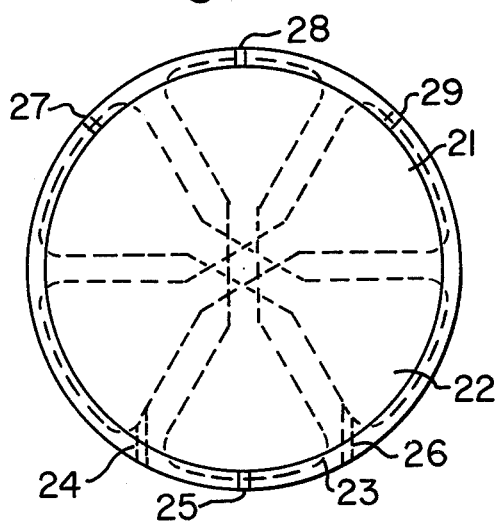
FIG. 5 is a front view of a flexible backing according to this invention having three separate and not interconnected compartments for defining three rigid plates within one backing. Each rigid plate being flexible relative to the others.

Referring now to FIG. 5, there is shown a variation of the embodiment illustrated in FIGS 1 to 4 in which the flexible backing plate 20 is provided with three rigid but separate sections 21, 22, and 23 each having its own inlet port 24, 25, and 26 and each having its own bleed 27, 28, and 29. The three compartments which when filled create three rigid sections are not interconnected. The backing according to this embodiment provides a limited amount of flexibility in the backing but in such a way to prevent the warping or collapse of the backing and curling of the edges. The backing according to this embodiment may be made from four thin plastic sheets thereof which are routed out to define the compartments before bonding together.

With either the embodiments as described with reference to FIG. 3 (i.e., elastic envelope backings) or the embodiments as described with reference to FIG. 4 (i.e., flexible plastic backings), it is essential that the rigidifying material occupies a volume sufficiently near the peripheral edge to prevent warping and curling of that edge.

Referring to FIG. 1, the backing piece 12 is designed to form a portion of a spherical shell having a concave portion which faces toward the chest wall after implantation and away from the soft implant. This design prevents rocking and makes the edges less palpable.

Figure 6:
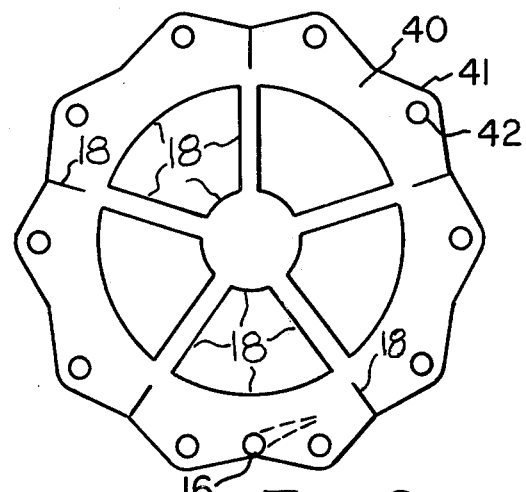
FIG. 6 is a preferred embodiment of a backing plate according to this invention having serrated edges and holes in the edges for tissue ingrowth.

Referring to FIG. 6, there is shown a backing piece 40 of the elastic envelope type with a serrated peripheral edge 41 and spaced tissue ingrowth openings 42. The serrated edges and/or ingrowth openings provide for better blend of the edges of the flexible backing piece into the chest wall or the pectoralis muscle. In this way it is less likely to be palpable through the skin and subcutaneous tissues. It is further preferred that the edges of the backing pice be tapered somewhat to reduce palpability; however, it is essential that the backing piece not be so tapered that after the rigidifying filler has been injected therein, it may still be warped and curled at the edges thereof. It may be desirable to provide fabric (Dacron) or other tissue ingrowth patches on the front and/or the back of the backing piece to promote blend of the backing piece with the surrounding environment and to prevent shifting relative to the chest wall and/or the pectoralis muscle and/or overlaying skin flaps.

Figure 7:
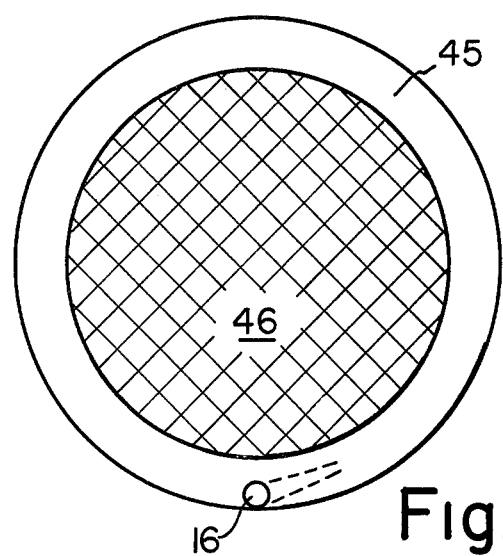
FIG. 7 is a front view of a backing according to this invention having a rigid annular portion in which the central portion of the backing is covered with a non-stretchable cloth.

Referring to FIG. 7, there is shown an embodiment of a backing piece according to this invention which has annular configuration 45. The inner portion is secured to a nonstretchable cloth 46 or cloth reinforced silicone elastomer or the like. This embodiment has the advantage of additional flexibility and contouring to the chest wall. The cloth 46 prevents the front envelope from working through the central opening. Thus, the collar 45 does not move up along the front envelope.

Figure 8:
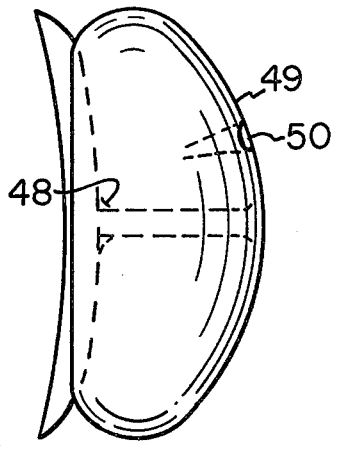
FIG. 8 is a side view of a preferred embodiment of this invention in which the port for injecting the material into the passageways of the backing is accessible through the soft envelope.

Referring now to FIG. 8, there is shown an embodiment of this invention in which the port 48 for injecting rigidifying material into the passageways in the backing is located centrally in the backing and is accessible through a passageway in the front envelope 49. This particular embodiment is useful for implants to be installed through a peri-aerolar incision where the envelope is of the inflatable type, the valve 50 for inflating same is provided centrally of the envelope as shown in the drawing. Applicant has not described the details of valves for filling the inflatable envelopes as these as known in the art.

Figure 9:
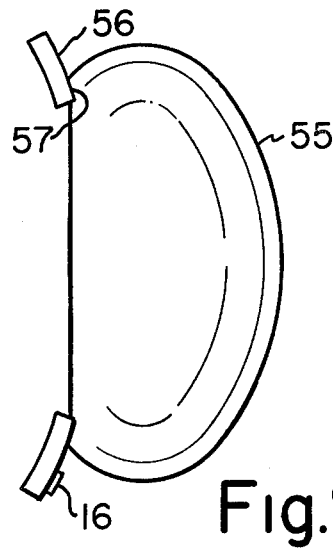
FIGS. 9 and 10 are sectioned side and front views respectively of a prosthesis according to this invention with a flexible backing in the shape of an annular portion of a spheroidal surface.
Figure 10:
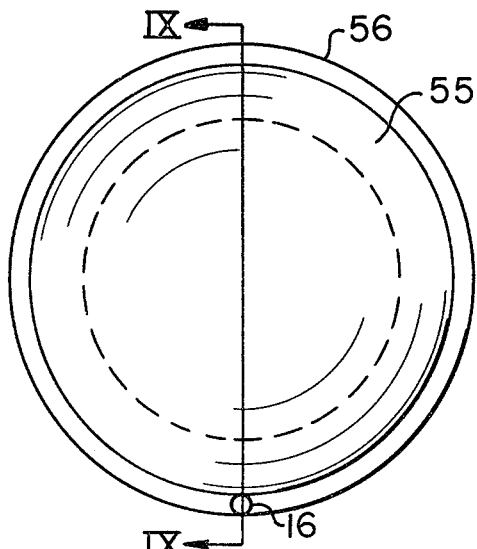

Referring to FIGS. 9 and 10, there is shown a preferred structure in which the front envelope 55 is secured to an annular rigid backing 56 at a location 57 near the inner annular edge thereof. The backing of the envelope 55 must be cloth reinforced.

Referring now to FIGS. 11 and 12, there is illustrated an embodiment of this invention wherein the backing has a second front envelope attached to the outer annular surface thereof. The second soft envelope is preferably a prefilled annular envelope 60 secured on the face of the backing 61. The primary front envelope 62 rests within the space circumscribed by the second annular envelope 60. The purpose of the second envelope 60 is to reduce the palpability of the edges of the collar.

Referring now to FIGS. 13 and 14, there is illustrated an embodiment of this invention wherein the front envelope of the prosthesis is secured to the backing and the edge of the front envelope is tapered so that the surface of the front envelope is substantially tangent to the backing at the outer edges thereof. This configuration is designed to minimize the palpability of the edges of the rigidified backing.

While it is desirable according to this invention to have the front envelope attached to the flexible backing, it is not necessary as after installation they will cooperate together to prevent the spherical contraction which results in many cases of mammary prosthesis implantation.

If it is necessary to remove the implant, it will be necessary to cut the rigidified backing into strips or the like. Thus the rigidifying material must be capable of being cut with, for example, a surgeon's common bone roungers. As already stated, applicant believes that at least methyl methacrylate bone cement will be a suitable rigidifying filler so long as its tendency to heat-up during curing is carefully considered. One cement of the type that would be a suitable filler material is sold under the trademark "Cranioplastic" by the L.D. Cauble Company and comprises a powdered portion comprised of methyl methacrylate polymer, methyl methacrylate-styrene copolymer and very small amounts of benzoyl peroxide and a liquid portion comprising methyl methacrylate monomer, ethylene dimethacrylate monomer and very small amounts of dimethyl p-toluidine and hydroquinon.

Another product of the type that would be used as a filler material is "Surgical Simplex P Radiopaque" bone cement sold by Howmedica International Ltd. and is described as methyl methacrylate, a mixture of polymethyl methacrylate, methyl methacrylate-styrene copolymer and barium sulfate. Yet another product that may be used as a filler material is room temperature vulcanizing (RTV) silicone rubber. There exist silicone gels which can be made to rigidify with application of heat, etc.

The filler material may comprise a product sold by 3M Corporation under the trade name "Concise Enamel Bond Resin." It comprises bisphenol-A glycidyl methacrylate, triethylene glycol dimethacrylate, methyl methacrylate, and a catalyst and an accelerator.

It should be understood that the backing could be prefilled with a rigidifible filler that can be activated or initiated to set by action external to the backing. Materials exist that are activated into setting by exposure to ultraviolet light. With an ultraviolet light source that can irradiate the material through the backing walls, the filler may be activated to become rigid as by setting up. The setting process is not immediate upon irradiation but is simply initiated by irradiating a portion of the material. The irradiation with ultraviolet may take place just before the backing is emplaced or after it is emplaced. It may only be necessary to irradiate a portion of the ultraviolet light sensitive filler and then the rigidifying reaction progresses to all contiguous parts of the filler. In this embodiment, the backing may be factory-filled and the port through which the filler was introduced will be permanently closed off at the factory.

Exemplary of the fillers that may be initiated from the outside of the backing envelope with ultraviolet light are the following: A product sold under the trade name "Nuva Seal" which comprises Bowen's Resin and benzoin methyl ether as an initiator that is activated by ultraviolet light. The ultraviolet light has been found to pass through the thin silicone walls of the backing envelope in sufficient amounts to activate this resin.

There also exist materials, e.g., silicones, that, when subjected to heat and/or pressure, activate to set or rigidify. The backing could be prefilled with these materials and placed in an autoclave for activation just prior to being emplaced.

Another technique for external actuation of the prefilled material inside the backing envelope is to provide the initiator or catalyst for the resin filler in a separate compartment separated from the remainder of the resin by an easily ruptured membrane. Prior to installation of the prosthesis, it is manipulated to rupture the membrane and to disperse the initiator among the remainder of the filler.

It should be understood that the rigidifying material need not be fluids or plastic masses but may comprise granular materials. The use of granular material is more practical with factory-prefilled backings than with backings filled just before or after emplacement.

Further, in the case of prefilled backings, the backing may comprise a flexible sheet or layer of rigidifible filler that is laminated between sheets of flexible silicone and sealed at the edges in a way to completely enclose the rigidifible sheet or layer. In other words, the flexible sheet of rigidifible material which, for example, may be activated by ultraviolet light, pressure or heat, is sandwiched between layers of materials that are inert to the body such as medical silicones. It is also contemplated that a flexible sheet or layer described above will not need to be encapsulated and sealed in silicone if, for example, it itself comprises a silicone or other biologically inert material. The basic concept of my invention is not changed by these embodiments. The prosthesis is provided with a backing which rigidifies in place. Thus, a small incision may be used and the backing can be molded to the chest wall. The rigidified backing then prevents the scar contracture from pulling the soft portion of the implant into a hard sphere or the like.

As used in the claims, "enclosed volume(s)" simply means passageway(s) or compartment(s) into which filler may be injected. By "rigid" or "rigidified" is meant resistant to substantial distortion by the scar tissue encapsulation process.

Having thus defined my invention in detail and with the particularity required by the Patent Laws, what is desired protected by Letters Patent is set forth in the following claims.

I claim:

1. A mammary prosthesis comprising a soft front envelope of an inert elastomer for containing an inert fluid material and a backing of an inert polymeric material, said backing being sized and defining at least one enclosed volume for receiving a material in said enclosed volume of said backing to rigidify the backing sufficiently to prevent the contraction of scar tissue around the prosthesis from pulling the prosthesis into a hard shape.

2. The mammary prosthesis according to claim 1 wherein the backing has at least one port into said enclosed volume such that a fluid material may be emplaced into the enclosed volume.

3. A mammary prosthesis according to claim 2 in which the backing defines more than one separate enclosed volume and ports associated with each, defining rigidifible segments which can be flexed relative to each other.

4. The mammary prosthesis according to claims 2 or 3 wherein the enclosed volume in the backing is provided with air bleeds.

5. The mammary prosthesis according to claim 2 wherein the port for introducing material to the backing is accessible through the bulk of the front envelope.

6. The mammary prosthesis according to claim 1 wherein said enclosed volume in the backing is prefilled with a rigidifiable filler, the setting of which can be activated by action external of the enclosed volume.

7. The mammary prosthesis acording to claim 1 in which the front envelope has a valve opening thereinto which permits the front envelope to be filled after implantation with an appropriate fluid.

8. The mammary prosthesis according to claim 1 in which the front envelope is prefilled with a soft gel.

9. The mammary prosthesis according to claims 1, 2, 6, 7 or 8 in which the front envelope and backing are made from a biologically inert silicone material.

10. The mammary prosthesis according to claim 1 in which the enclosed volume in the backing comprises at least an annular passageway near the outer edge of the backing.

11. The mammary prosthesis according to claims 1 or 10 in which the enclosed volume in the backing comprises radially extending passageways therein.

12. The mammary prosthesis according to claim 1 in which the backing is an annular rigid disc having passages therein and a non-stretching flexible center portion.

13. The mammary prosthesis according to claims 1, 2, 6 or 12 in which the face of the backing is larger than the back of the front envelope and extends outwardly of the front envelope to defin a collar.

14. The mammary prosthesis according to claims 1, 2 or 6 in which the backing has a concaved configuration with the concaved surface facing away from the front envelope.

15. The mammary prosthesis according to claims 1, 2, 6 or 12 wherein the backing is provided with serrated edges.

16. The mammary prosthesis according to claims 1, 2, 6 or 12 wherein tissue ingrowth holes are provided along the edges of the backing.

17. The mammary prosthesis according to claims 1, 2 or 6 wherein the backing is an annular disc to which the front envelope is attached near the inner annular edge thereof and wherein the back of the front envelope is reinforced to be non-stretchable.

18. The mammary prosthesis according to claims 1, 2 or 6 wherein the backing has attached to the face thereof an annular soft envelope near the outer edges thereof.

19. A mammary prosthesis according to claims 1, 2 or 6 in which the soft front implant envelope is tapered at the outer edges so that the surface of the soft implant is substantially tangent to the rigidifible flexible backing at the outer edges thereof.

20. A mammary prosthesis according to claims 1, 2 or 6 wherein the backing is shaped to face the entire back surface of the front envelope.

21. A mammary prosthesis according to claims 1, 2 or 6 wherein the backing is shaped to face at least the lower half of the back surface of the front envelope.

22. A mammary prosthesis according to claims 1, 2 or 6 wherein the backing is shaped to face at least the lower half of the back surface of the front envelope and to provide a collar outwardly of the front envelope along at least the lower half of the back surface of the front envelope.

23. A mammary prosthesis according to claim 1 wherein the backing comprises an envelope of flexible elastomer having two large faces joined at the periphery thereof and also having a plurality of elongate quilt-like joins between the faces.

24. A mammary prosthesis according to claim 1 wherein the backing comprises a flexible plastic disc having a network of passageways therein defining the said enclosed volume.

25. A method of providing a mammary prosthesis comprising the steps for
 (a) surgically emplacing a prosthesis comprising a soft front envelope and a flexible backing defining an enclosed volume,
 (b) injecting rigidifying materials into the said enclosed volume to rigidify the backing.

26. A method according to claim 25 wherein the soft front envelope is of the prefilled type.

27. A method according to claim 25 wherein the soft front envelope is of the inflatable type and the further step for
 (c) aspirating and inflating with an appropriate fluid the front envelope.

28. The method according to claim 25 wherein the rigidifying material hardens and the further step for
 (d) shaping the backing to the underlying anatomy while it is in the process of hardening.

29. A method of providing a mammary prosthesis comprising the steps for
 (a) surgically emplacing a prosthesis comprising a soft front envelope and a flexible backing defining an enclosed volume filled with rigidifying materials,
 (b) activating the rigidifying materials to harden at about the time of emplacing the prosthesis.

30. The method according to claim 29 wherein the soft front envelope is of the prefilled type.

31. A method according to claim 29 wherein the soft front envelope is of the inflatable type and the further step for
 (c) aspirating and inflating with an appropriate fluid the front envelope.

32. The method according to claim 29 comprising the further step for
 (d) shaping the backing to the underlying anatomy while it is in the process of hardening.

33. A mammary prosthesis comprising a soft front envelope of an inert elastomer for containing an inert fluid material and a backing of inert polymeric material being sufficiently rigid and of a shape to prevent the contracture of scar tissue around the prosthesis from pulling the prosthesis into a hard shape by providing a natural flow space into which the fluid material may be displaced after the scar contracture has taken place.

* * * * *